United States Patent [19]

Franckowiak et al.

[11] 4,280,998

[45] Jul. 28, 1981

[54] 1,4-DIHYDROPYRIDAZINE-3-CARBOXYLIC ACID DERIVATIVES, A PROCESS FOR THEIR PREPARATION AND THEIR USE AS ANTIHYPERTENSIVES

[75] Inventors: Gerhard Franckowiak; Friedrich Bossert; Arend Heise; Robertson Towart, all of Wuppertal, Fed. Rep. of Germany

[73] Assignee: Bayer Aktiengesellschaft, Leverkusen, Fed. Rep. of Germany

[21] Appl. No.: 58,590

[22] Filed: Jul. 18, 1979

[30] Foreign Application Priority Data

Aug. 8, 1978 [DE] Fed. Rep. of Germany ....... 2834624

[51] Int. Cl.³ .................... A61K 31/50; C07D 237/04; C07D 409/04; C07D 401/04

[52] U.S. Cl. .................................. 424/250; 544/224; 544/235; 544/238; 560/22; 560/23; 568/306; 568/307; 546/335; 549/76

[58] Field of Search ................. 544/224, 238; 424/250

[56] References Cited

PUBLICATIONS

Frank—Neumann et al., Chem. Abs. 71, 81259g (1969).

*Primary Examiner*—Mark L. Berch
*Attorney, Agent, or Firm*—Sprung, Felfe, Horn, Lynch & Kramer

[57] ABSTRACT

The invention relates to 1,4-dihydro-pyridazine-3-carboxylic acid derivatives and compositions containing said derivatives. Also included in the invention are methods for the manufacture and use of said compounds and compositions. The derivatives of the invention influence the circulation and have a spasmolytic and anti-inflammatory action.

14 Claims, No Drawings

1,4-DIHYDROPYRIDAZINE-3-CARBOXYLIC ACID DERIVATIVES, A PROCESS FOR THEIR PREPARATION AND THEIR USE AS ANTIHYPERTENSIVES

The present invention relates to new 1,4-dihydropyridazine-3-carboxylic acid derivatives, to a process for their production and to their use as medicaments which have an influence on the circulation and which have a spasmolytic and anti-inflammatory action.

It has already been disclosed that 1,4-dihydropyridazines are obtained when substituted 1,4-dicarbonyl compounds are reacted with hydrazine hydrate (compare W. Borsche and M. Spannagel, Liebigs Ann. Chem. 331, 300 (1904)). However, according to experience, there are limits to the ease of preparation of such 1,4-dicarbonyl compounds if several carbonyl groups are introduced into the molecule by ester and acyl substituents. Surprisingly, the reaction of such compounds, as assumed intermediate stages of the reaction, in situ with hydrazines to give the 1,4-dihydropyridazine-3-carboxylic acid esters according to the invention has now been successful.

According to the present invention there are provided compounds which are 1,4-dihydropyridazine-3-carboxylic acid derivatives of the general formula

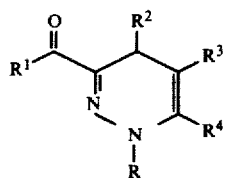

in which
R denotes a hydrogen atom or a straight-chain or branched alkyl radical which is optionally interrupted in the chain by one or two oxygen atoms, or an aryl or aralkyl radical,
$R^1$ denotes an alkyl, aryl or aralkyl radical or a group of the formula

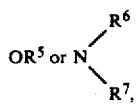

in which
$R^5$ denotes a hydrogen atom or a straight-chain, branched or cyclic, saturated or unsaturated aliphatic hydrocarbon radical which is optionally interrupted in the chain by 1 or 2 oxygen or sulphur atoms and/or which is optionally substituted by hydroxyl or halogen or by a phenoxy or phenyl group which is optionally substituted by halogen, cyano, amino, alkylamino, alkoxy, alkyl, trifluoromethyl or nitro, or by an α-, β- or γ-pyridyl group or by an amino group, this amino group optionally carrying either hydrogen and one substituent or two identical or different substituents selected from alkyl, alkoxyalkyl, aryl and aralkyl, and these substituents optionally forming, with the nitrogen atom, a 5-membered to 7-membered ring which can contain an oxygen, sulphur or nitrogen atom as a further hetero-atom, or $R^5$ denotes an aryl group which is optionally substituted by one or two identical to different substituents selected from alkyl, alkoxy, aryl, aralkyl, halogen, nitro, cyano, trifluoromethyl, trifluoromethoxy, amino and mono- and di- alkylamino, $R^6$ denotes a hydrogen atom or an alkyl, aryl, aralkyl, thienyl, furyl or pyridyl radical which optionally carries 1 to 3 identical or different substituents selected from halogen, nitro, cyano, trifluoromethyl, trifluoromethoxy, alkoxy, alkyl and dialkylamino and $R^7$ denotes a hydrogen atom or an amino or mono- or dialkylamino group, or has a meaning given for radical $R^6$, without being identical to $R^6$; or $R^6$ and $R^7$ together form a 5-membered to 7-membered ring which optionally contains, as a heteroatom, oxygen or sulphur, or a group —NH or —N-alkyl, $R^2$ denotes an aryl radical or a thienyl, furyl, pyrryl, pyrazolyl, imidazolyl, oxazolyl, isooxazolyl, thiazolyl, pyridyl, pyridazinyl, pyrimidyl, pyrazinyl, quinolyl, isoquinolyl, indolyl, benzimidazolyl, quinazolyl or quinoxalyl radical, the aryl radical and the heterocyclic radicals optionally containing 1 to 3 identical or different substituents selected from phenyl, alkyl, alkoxy, alkylene, dioxyalkylene, halogen, trifluoromethyl, cyano, trifluoromethoxy, hydroxyl, nitro, azido, carboxyl, carbalkoxy, carboxamido, sulphonamido, $SO_2$-alkyl and $SO_2$-trifluoroalkyl, $R^3$ denotes a hydrogen atom or a group of the formula $COR^8$,
in which
$R^8$ denotes an alkyl, aryl or aralkyl radical or a group of the formula $OR^9$,
in which
$R^9$ has a meaning given for radical $R^5$, but need not be identical to $R^5$, and
$R^4$ denotes a straight-chain or branched alkyl radical in which a hydrogen is replaced by a hydroxyl, acyloxy or aminoacyl group, or a polyfluoroalkyl radical or an aryl, aralkyl, thienyl, furyl, pyrryl or pyridyl radical, which optionally carries 1 to 3 identical or different substituents, it being possible for $R^4$ and $R^8$ to together form a 5-membered to 7-membered ring which optionally contains an oxygen as a hetero-atom.

In the definitions given above defining substituents in Formula (I) and in the definitions for said substituents where indicated below, the following preferred values will apply unless otherwise specifically indicated:
alkyl and alkoxy groups contain 1-8 carbon atoms
aryl or aralkyl groups are mono- or bi-cyclic carbocyclic, such as phenyl, bi-phenyl or naphthyl and the alkyl portion of aralkyl groups contains preferably 1-4, more preferably 1-2 carbon atoms.
where said aryl or aralkyl groups are substituted on the aryl portion, the number of substituents can be up to 5, preferably up to 3 and particularly 1 or 2
halogen atoms are preferably fluoro, chloro or bromo.

The compounds according to the invention represent a novel class of substances for treatment of the circulation and for treatment of the gastro-intestinal tract, the urogenital tract and the respiratory system, and also have an anti-inflammatory action. On the basis of their circulation-influencing, spasmolytic and anti-inflammatory action, they can be used as antihypertensive agents, as vasodilators, as coronary therapeutics, as spasmolytic agents and as antiphlogistic agents.

According to the present invention there is further provided a process for the production of compounds of the present invention in which a nitronic acid of the general formula

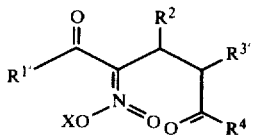

in which
R$^{1'}$ denotes an alkyl, aryl or aralkyl radical or a group of the general formula OR$^{5'}$,
in which
R$^{5'}$ denotes a straight-chain, branched or cyclic saturated hydrocarbon radical which is optionally interrupted in the chain by one or two oxygen atoms or a sulphonyl group or substituted by one or more halogen atoms, or in which a hydrogen atom is optionally replaced by a hydroxyl group or by a phenoxy or phenyl group which is optionally substituted by halogen, hydroxyl, alkoxy, alkyl, trifluoromethyl, trifluoromethoxy, nitro or cyano, or by an α-, β- or γ-pyridyl group, or
R$^{5'}$ denotes an aryl group which is optionally substituted by one or two identical or different substituents selected from alkyl, aryl, aralkyl, alkoxy, halogen, nitro, trifluoromethyl and trifluoromethoxy,
R$^{3'}$ denotes a hydrogen atom or a group of the formula COR$^{8'}$,
in which
R$^{8'}$ denotes an alkyl, aryl or aralkyl radical or a group of the formula OR$^{9'}$,
in which
R$^{9'}$ has a meaning given for radical R$^{5'}$, but need not be identical to R$^{5'}$,
R$^{2}$ and R$^{4}$ have the above-mentioned meanings and
X denotes a cation such as a hydrogen ion or an alkali metal, ammonium or alkylammonium ion, is first reacted with ozone (compare N. Kornblum and P. A. Wade. J. Org. Chem. 38 (1418 et seq. (1973)) and then with a hydrazine of the general formula

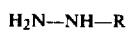

in which
R has the above-mentioned meaning,
in an inert organic solvent.

Derivatives can optionally be formed from the resulting compounds by generally known methods of saponification, esterification, trans-esterification or amidation to give further compounds of the formula (I) according to the invention.

If the sodium salt of 2-acetyl-4-aci-nitro-3-(2-nitrophenyl)-glutaric acid diethyl ester, ozone and hydrazine are used as starting substances, the course of the reaction can be represented by way of example by the equation which follows:

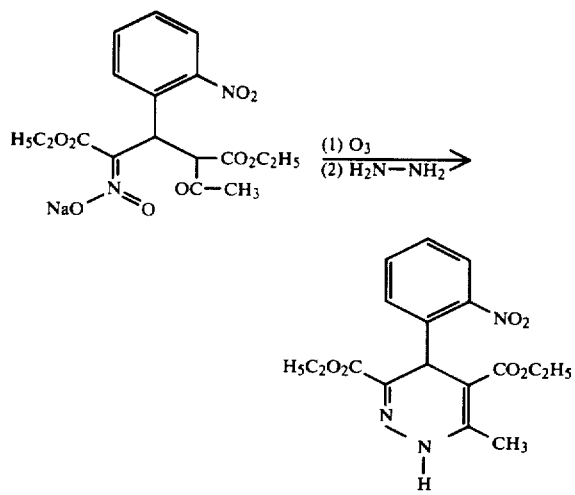

According to the procedure indicated, a nitronic acid of the formula (II) (X=H) or a salt thereof is first reacted with ozone and the product is then reacted with a hydrazine derivative of the formula (III) to give a 1,4-dihydropyridazine derivative of the formula I.

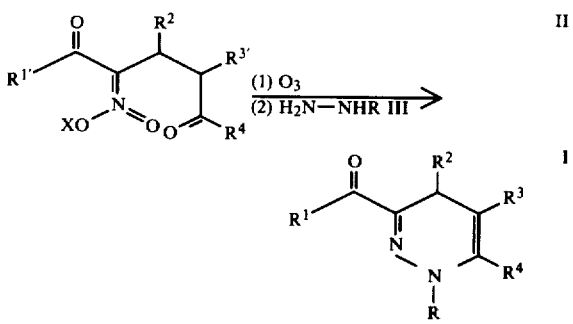

Preferred compounds of formula II (which yield the corresponding compounds of formula I when reacted with ozone and a hydrazine, H$_2$N-NHR in which R is defined as above) are those in which
R$^{1'}$ denotes a straight-chain or branched saturated alkyl radical with 1 to 4, in particular 1 to 2, carbon atoms, an aryl radical, in particular a phenyl radical which is substituted by cyano, nitro, halogen or methoxy, or an aralkyl radical, in particular a benzyl radical, or a hetaryl radical, in particular a thienyl, furyl or pyridyl radical, or the group OR$^{5'}$,
R$^{5'}$ denotes a straight-chain, branched or cyclic saturated hydrocarbon radical with up to 8, in particular with up to 6, carbon atoms, which is optionally interrupted in the chain by one or two oxygen atoms or a sulphonyl group or/and in which hydrogen atoms are optionally replaced by a hydroxyl group or halogen, preferably one or more fluorine atoms, or by a phenoxy or phenyl group which is optionally substituted by halogen, such as fluorine, chlorine or bromine, or cyano, alkoxy with 1 to 4 carbon atoms, alkyl with 1 to 4 carbon atoms, trifluoromethyl or nitro, or by an α-, β- or γ-pyridyl group, or
R$^{5'}$ denotes an aryl radical, in particular a phenyl radical, which can optionally carry 1 to 2 identical or different substituents, such as straight-chain or branched alkyl with 1 to 4 carbon atoms, halogen, such as fluorine, chlorine or bromine, or nitro, cyano, trifluoromethyl or trifluoromethoxy.

$R^2$ denotes a phenyl or naphthyl radical or a thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl radical; the heterocyclic radicals mentioned and, in particular, the phenyl radical optionally contains 1 or 2 identical or different substituents, preferred substituents being phenyl, straight-chain or branched alkyl with 1 to 8, in particular 1 to 4 carbon atoms, cycloalkyl with 3 to 7 carbon atoms, alkoxy with preferably 1 to 4, in particular 1 to 2, carbon atoms, dioxymethylene, halogen, such as fluorine, chlorine, bromine or iodine, in particular fluorine, chlorine or bromine, trifluoromethyl, trifluoromethoxy, cyano, nitro, azido, hydroxyl, carboxyl, carbalkoxy with preferably 2 to 4, in particular 2 or 3, carbon atoms, carboxamido, sulphonamido or $SO_2$-alkyl, alkyl preferably containing 1 to 4, in particular 1 or 2, carbon atoms, $R^{3'}$ denotes a hydrogen atom or a group of the formula $COR^{8'}$, in which $R^{8'}$ denotes a straight-chain or branched alkyl radical, preferably with 1 to 4 carbon atoms, or a phenyl or benzyl radical, or in which $R^{8'}$ denotes a group of the formula $OR^{9'}$, in which $R^{9'}$ has a meaning given for radical $R^{5'}$, but need not be identical to $R^{5'}$, $R^4$ denotes a straight-chain or branched alkyl radical with 1 to 4, in particular 1 to 2, carbon atoms, it being possible for $R^4$ and $R^{8'}$ to together form a 5-membered to 7-membered, preferably a 5-membered or 6-membered, ring which optionally contains an oxygen atom as a hetero-atom, or $R^4$ denotes a perfluoroalkyl radical with, in particular, 1 to 2 carbon atoms, a phenyl radical which is optionally substituted by a nitro or methoxy group, or an alkyl radical, in particular a benzyl radical, or a hetaryl radical, in particular a thienyl, furyl or pyridyl radical, and X denote a monovalent cation, such as a hydrogen, alkylammonium or alkali metal ion, in particular a sodium or potassium ion.

The nitronic acids and salts thereof used according to the invention as starting substances can be prepared, for example, by a base-catalysed Michael addition of nitroacetic acid esters onto ylidene-carbonyl compounds (compare A. Dornow and A. Frese, Ann. Chem. 578, 122 (1952)).

Examples of starting substances of Formula II which may be mentioned are: 2-aci-nitro-3-(3-nitrophenyl)-5-oxo-hexanoic acid ethyl ester, the sodium salt of 2-aci-nitro-5-oxo-3-(2-trifluoromethylphenyl)-heptanoic acid cyclopentyl ester, the diethylammonium salt of 4-acetyl-2-aci-nitro-4-(3-chlorophenyl)-5-oxo-hexanoic acid ethyl ester, the sodium salt of 2-acetyl-4-aci-nitro-3-(2-methylsulphonylphenyl)-glutaric acid 1-n-butyl 5-methyl ester, the sodium salt of 2-acetyl-4-aci-nitro-3-(3,4-dioxymethylenephenyl)-glutaric acid 5-methyl 1-($\beta,\beta'$-hexafluoroisopropyl) ester, the sodium salt of 2-acetyl-4-aci-nitro-3-(3-bromophenyl)-glutaric acid di-($\beta$-trifluoroethyl) ester, the sodium salt of 2-acetyl-4-aci-nitro-3-(2-carboxyethylphenyl)-glutaric acid diethyl ester, the sodium salt of 2-acetyl-4-aci-nitro-3-(2-trifluoromethylsulphonyl-phenyl)-glutaric acid di-($\beta$-n-butoxyethyl) ester, the sodium salt of 2-acetyl-4-aci-nitro-3-(3-chlorophenyl)-glutaric acid 5-($\beta$-phenylethyl) 1-ethyl ester, the sodium salt of 2-acetyl-4-aci-nitro-3-(2-trifluoromethylphenyl)-glutaric acid 1-($\beta$-2-chlorophenoxyethyl)-ethyl ester, the sodium salt of 2-acetyl-4-aci-nitro-3-(3-nitrophenyl)-glutaric acid 5-i-propyl 1-($\beta$-pyrid-3-yl-ethyl) ester, the sodium salt of 2-acetyl-4-aci-nitro-3-(3-trifluoromethylphenyl)-glutaric acid 1-ethyl 5-($\beta$-phenylsulphonylethyl) ester, the sodium salt of 2-acetyl-4-aci-nitro-3-pyrid-4-yl-glutaric acid 1-($\beta$-methoxyethyl) 5-methyl ester, the sodium salt of 2-acetyl-4-aci-nitro-3-naphth-1-yl-glutaric acid dimethyl ester, the sodium salt of 2-acetyl-4-aci-nitro-3-pyrr-2-yl-glutaric acid diethyl ester, the sodium salt of 2-acetyl-4-acid-nitro-3-fur-2-yl-glutaric acid 1-ethyl 5-methyl ester and the sodium salt of 2-acetyl-4-aci-nitro-3-(4-phenylphenyl)-glutaric acid 5-methyl 1-($\beta$-trifluoroethyl) ester.

Preferred compounds of formula (III) are those in which R denotes a hydrogen atom or a straight-chain or branched alkyl radical with 1 to 8 carbon atoms, in particular 1 to 4 carbon atoms, the alkyl radical optionally being interrupted in the alkyl chain by an oxygen atom, or a phenyl radical, or an aralkyl radical, in particular a benzyl radical.

Examples of compounds of the formula (III) which may be mentioned are: hydrazine; hydrazine hydrate; alkyl hydrazines and alkoxy hydrazines having 1 to 4 carbon atoms, such as methylhydrazine, ethylhydrazine, isopropylhydrazine, n-butylhydrazine, isobutylhydrazine, methoxyethylhydrazine; phenyl-lower alkyl hydrazines in which the alkyl portion has 1 to 4 carbon atoms; benzylhydrazine, $\beta$-phenylethylhydrazine and phenylhydrazine.

Specifically contemplated and included in the invention is each specific compound of above-identified Formula (I) obtained by reaction of each of the above-identified specific nitronic acids of Formula (II) with ozone and each of the above-identified specific hydrazines of Formula (III).

The hydrazines used as starting substances are known from the literature, or they can be prepared by methods which are known from the literature (literature: L. F. Andrieth and B. A. Ogg, The Chemistry of Hydrazine, John Wiley and Sons. Inc. New York, N.Y. 1951).

Possible diluents are all the inert organic solvents. These include, preferably, alcohols, such as ethanol, methanol and isopropanol, ethers, such as dioxane, diethyl ether, tetrahydrofurane, glycol monomethyl ether or glycol dimethyl ether, or dimethylformamide, dimethylsulphoxide, acetonitrile, pyridine and hexamethylphosphoric acid triamide.

The reaction temperatures can be varied within a substantial range. In general, the reaction is carried out between $-120°$ C. and $+120°$ C., preferably in the range between $-80°$ and $+20°$ C.

The reaction can be carried out under normal pressure, but also under elevated pressure. In general, it is carried out under normal pressure.

In carrying out the process according to the invention, 1 mol of the compound of the formula (II) is first ozonised at a low temperature in a suitable solvent and the product is then reacted with one mol of the hydrazine compound of the formula (III) at room temperature.

Isolation and purification of the substances according to the invention is preferably effected by a procedure in which, if appropriate after separating off insoluble substances, the solvent is distilled off in vacuo and the product, which may only be obtained in the crystalline form after chromatography, is recrystallised from a suitable solvent.

In addition to the process described above, further derivatives according to the invention can appropriately be prepared, by saponification, esterification, transesterification or amidation methods which are known from the literature (compare Organikum, VEB Deutscher Verlag der Wissenschaften, Berlin 1967), from the 1,4-dihydropyridazine- mono- and -di-carboxylic acid esters accessible by the process according to the invention.

The following processes may be listed, merely by way of illustration, in this context:

(a) Saponification 1,4-Dihydropyridazine-3-carboxylic acid esters (formula I, $R^1=OR^5$) and -3,5-dicarboxylic acid esters (formula I, $R^1=OR^5$, $R^3=COOR^8$) can be selectively saponified with one equivalent of an alkali to give the 1,4-dihydropyridazine-3-carboxylic acids (formula I, $R^1=OH$). Saponification with an excess of alkali leads to the 1,4-dihydropyridazine-3,5-dicarboxylic acids (formula I, $R^1=OH$, $R^3=COOH$).

(b) Esterification 1,4-Dihydropyridazine-3-carboxylic acids (formula I, $R^1=OH$), 1,4-dihydropyridazine-3,5-dicarboxylic acid half-esters (formula I, $R^1=OH$, $R^3=COOR^8$ or $R^1=OR^5$, $R^3=COOH$) and 1,4-dihydropyridazine-3,5-dicarboxylic acids (formula I, $R^1=OH$, $R^3=COOH$) can be reacted with alcohols, diazoalkanes, dialkyl sulphates or alkyl halides to give the corresponding esters (formula I, $R^1=OR^5$ or $R^1=OR^5$, $R^3=COOR^8$).

(c) Trans-esterification 1,4-Dihydropyridazine-3-carboxylic acid esters (formula I, $R^1=OR^5$) and -3,5-dicarboxylic acid esters (formula I, $R^1=OR^5$, $R^3=COOR^8$) can be reacted in alcohols under acid or base catalysis to give the corresponding esters.

(d) Amidation 1,4-Dihydropyridazine-3-carboxylic acids (formula I, $R^1=OH$), 1,4-dihydropyridazine-3-carboxylic acid esters (formula I, $R^1=OR^5$), 1,4-dihydropyridazine-3,5-dicarboxylic acid half-esters (formula I, $R^1=OH$, $R^3=COOR^8$ or $R^1=OR^5$, $R^3=COOH$), 1,4-dihydropyridazine-3,5-dicarboxylic acids (formula I, $R^1=OH$, $R^3=COOH$) and 1,4-dihydropyridazine-3,5-dicarboxylic acid esters (formula I; $R^1=OR^5$, $R^3=COOR^8$) can be converted into the corresponding amides or hydrazides (formula I, $R^1=NR^6R^7$ or $R^1=NR^6R^7$, $R^3=COOR^8$ or $R^1=OR^5$, $R^3=CONR^6R^7$ or $R^1=NR^6R^7$, $R^3=CONR^6R^7$) with primary or secondary aliphatic or atomatic amines or hydrazines in suitable solvents.

Of course, these processes may be used, with other of the specified meanings for the radicals, for the preparation of other compounds according to the invention.

The compounds according to the invention exist in stereoisomeric forms which either behave as mirror images (enantiomers) or do not behave as mirror images (diastereomers). The present invention relates to both the antipodes and the racemic forms, as well as the diastereomer mixtures. The racemic forms, like the distereomers, can be separated into constituents which are single stereoisomers in a known manner (compare, for example, E. L. Eliel, Stereochemistry of Carbon Compounds, McGraw Hill, 1962).

Thus, for example racemate mixtures can be separated into the pure racemates in a known manner on the basis of the physicochemical differences of the constituents, for example by chromatography and/or fractional crystallisation.

Pure racemates can be resolved according to known methods, for example by recrystallisation from an optically active solvent, with the aid of micro-organisms or by reaction with an optically active acid or base which forms salts with the racemic compound and separation of the salts obtained in this manner, for example on the basis of their different solubilities, into the diastereomers from which the antipodes can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end products in the form of the pure racemates or optical antipodes by employing starting substances, containing one or more asymmetrical C atoms, in the form of the pure racemates or optical antipodes.

Compounds of the formula (I) which are of particular interest are those in which R denotes a hydrogen atom or a methyl, phenyl or benzyl radical, $R^1$ denotes a methyl, phenyl, nitrophenyl, chlorophenyl or benzyl radical or a group of the formula

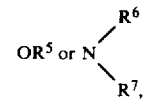

in which $R^5$ denotes a straight-chain, branched or cyclic alkyl, alkenyl or alkinyl radical with up to 8 carbon atoms, the alkyl or alkylene chain optionally being interrupted by an oxygen and/or sulphur atom and/or substituted by halogen, in particular one or more fluorine atoms, or by phenoxy, phenyl, halogenophenyl, nitrophenyl, pyridyl, furyl or thienyl, or denotes a pyridyl, furyl, thienyl or a phenyl radical which is optionally substituted by one or two identical or different substituents selected from halogen, nitro, cyano, trifluoromethyl, trifluoromethoxy and alkyl or alkoxy with in each case 1 to 4, in particular with 1 to 2, carbon atoms, $R^6$ denotes a hydrogen atom or a methyl, ethyl, benzyl, pyridyl or phenyl radical which is optionally substituted by one or two identical or different substituents selected from halogen, nitro, cyano, trifluoromethyl or trifluoromethoxy, $R^7$ denotes a hydrogen atom or an amino or mono- or dialkylamino group with 1 to 4, in particular 1 to 2, carbon atoms per alkyl group, or has a meaning given for radical $R^6$, without being identical to $R^6$; or $R^6$ and $R^7$ together form a 5-membered to 7-membered, in particular a 5-membered or 6-membered, ring, which can furthermore contain an oxygen atom or an NH group or an N-alkyl group with 1 to 4 carbon atoms, $R^2$ denotes a phenyl radical which is optionally substituted by one or two identical or different substituents selected from nitro, halogen, azido, cyano, trifluoromethyl, trifluoromethoxy and alkyl or alkoxy with in each case 1 to 4, in particular with 1 to 2, carbon atoms, or denotes a pyridyl, thienyl or furyl radical, $R^3$ denotes a hydrogen atom or a group of the formula $COR^8$, in which $R^8$ denotes an alkyl radical with 1 to 4 carbon atoms or an aryl radical, or $R^8$ and $R^4$ together form a 5-membered or 6-membered ring, optionally with a hetero-atom, such as oxygen, or $R^8$ denotes a group of the formula $OR^9$, in which $R^9$ has a meaning given for radical $R^5$, but need not be identical to $R^5$, and $R^4$ denotes an alkyl radical with 1 to 2 carbon atoms, which optionally forms the above-mentioned ring with $R^8$, or denotes a phenyl, benzyl, pyridyl or thienyl radical.

The following active compounds according to the invention may be mentioned, in addition to the preparation examples given below: 6-ethyl-1,4-dihydro-4-(3-nitrophenyl)-pyridazine-3-carboxylic acid ethyl ester, 1,4-dihydro-4-fur-2-yl-6-methylpyridazine-3-carboxylic acid cyclopentyl ester, 5-acetyl-1,4-dihydro-6-methyl-4-(4-trifluoromethylphenyl)-pyridazine-3-carboxylic acid methyl ester, 5-benzoyl-4-(3-chlorophenyl)-1,4-dihydro-6-methylpyridazine-3-carboxylic acid methyl ester, 1,4-dihydro-6-methyl-4-(2-methylsulphonylphenyl)-pyridazine-3,5-dicarboxylic acid 5-n-butyl 3-methyl ester, 1,4-dihydro-6-methyl-4-(3-trifluoromethoxyphenyl)-pyridazine-3,5-dicarboxylic acid 5-ethyl 3-isopropyl ester, 1,4-dihydro-6-methyl-4-(2-trifluoromethoxyphenyl)-pyridazine-3,5-dicarboxylic acid 5-($\beta,\beta'$-hexafluoroisopropyl) 3-($\beta$-trifluoro-ethyl) ester, 4-(3-cyanophenyl)-1,4-dihydro-1,6-dimethyl-pyridazine-3,5-dicarboxylic acid 5-i-butyl 3-n-propyl ester, 4-(2,6-dichlorophenyl)-1,4-dihydro-6-methyl-pyridazine-3,5-dicarboxylic acid dimethyl ester, 4-(2-chlorophenyl)-1,4-dihydro-6-trifluoromethyl-pyridazine-3,5-dicarboxylic acid dimethyl ester, 1,4-dihydro-4-(3-ethylphenyl)-6-methyl-pyridazine-3,5-dicarboxylic acid di-($\beta$-n-butoxyethyl)ester, 1,4-dihydro-4-(3,4-dioxymethylenephenyl)-6-methyl-pyridazine-3,5-dicarboxylic acid diethyl ester, 4-(3-bromophenyl)-1,4-dihydro-6-methyl-pyridazine-3,5-dicarboxylic acid di-($\beta$-methoxyethyl) ester, 4-(4-carboxyethylphenyl)-1,4-dihydro-6-methyl-pyridazine-3,5-dicarboxylic acid diethyl ester, 1,4-dihydro-6-methyl-4-(2-trifluoromethylsulphonylphenyl)-pyridazine-3,5-dicarboxylic acid di-($\beta$-trifluoroethyl) ester, 1,4-dihydro-6-methyl-4-(3-nitrophenyl)-1-phenyl-pyridazine-3,5-dicarboxylic acid 3-ethyl 5-methyl ester, 4-(3-chlorophenyl)-1,4-dihydro-6-methyl-pyridazine-3,5-dicarboxylic acid 3-ethyl 5-($\beta$-phenylethyl) ester, 1,4-dihydro-6-methyl-4-(2-nitrophenyl)-pyridazine-3,5-dicarboxylic acid 5-($\beta$-3-chlorophenylethyl) 3-ethyl ester, 1,4-dihydro-6-ethyl-4-(2-nitrophenyl)-pyridazine-3,5-dicarboxylic acid 3-ethyl 5-($\beta$-pyrid-2-yl-ethyl) ester, 1,4-dihydro-4-(3-methoxyphenyl)-6-methyl-pyridazine-3,5-dicarboxylic acid 3-methyl 5-($\beta$-phenylsulphonylethyl) ester, 1,4-dihydro-6-methyl-4-pyrid-4-yl-pyridazine-3,5-dicarboxylic acid di-($\beta$-methoxyethyl) ester, 1,4-dihydro-6-methyl-4-(2-nitrophenyl)-pyridazine-3,5-dicarboxylic acid diallyl ester, 4-(2-chlorophenyl)-1,4-dihydro-6-methyl-pyridazine-3,5-dicarboxylic acid 3-propargyl 5-n-propoxyethyl ester, 1,4-dihydro-6-methyl-4-(2-trifluoromethylphenyl)-pyridazine-3,5-dicarboxylic acid 3-($\beta$-dimethylaminoethyl) 5-($\beta$-trifluoroethyl) ester, 1,4-dihydro-6-methyl-4-(3-trifluoromethylphenyl)-pyridazine-3,5-dicarboxylic acid 3-($\beta$-N-3-nitrophenyl-N-methylaminoethyl) 5-benzyl ester, 1,4-dihydro-6-methyl-4-(3-trifluoromethylphenyl)-pyridazine-3,5-dicarboxylic acid 3-($\beta$-N-morpholinoethyl) 5-ethyl ester, 1,4-dihydro-6-methyl-4-pyrid-2-yl-pyridazine-3,5-dicarboxylic acid 3-ethyl 5-methyl ester, 1,4-dihydro-6-methyl-4-pyrr-2-yl-pyridazine-3,5-dicarboxylic acid 3-ethyl 5-methyl ester, 1,4-dihydro-6-methyl-4-naphth-1-yl-pyridazine-3,5-dicarboxylic acid dimethyl ester, 4-(3,4-dichlorophenyl)-1,4-dihydro-6-methyl-pyridazine-3,5-dicarboxylic acid diisopropyl ester, 1,4-dihydro-4-(3,5-dinitrophenyl)-6-methylpyridazine-3,5-dicarboxylic acid diethyl ester, 4-(3-chloro-4-methylphenyl)-1,4-dihydro-6-methylpyridazine-3,5-dicarboxylic acid 3-ethyl 5-methyl ester, 1,4-dihydro-6-methyl-4-(2-nitrophenyl)-pyridazine-3,5-dicarboxylic acid 5-t-butyl 3-phenyl ester, 3-carbazoyl-1,4-dihydro-6-methyl-4-(3-nitrophenyl)-pyridazine-5-carboxylic acid benzyl ester, 1,4-dihydro-6-methyl-3-(4-methylpiperazinylcarbonyl)-4-tolu-3-yl-pyridazine-5-carboxylic acid isopropyl ester, 4-(3-chlorophenyl)-1,4-dihydro-6-methyl-3-(3-nitrophenylcarbamoyl)-pyridazine-5-carboxylic acid n-propyl ester, 1,4-dihydro-6-methyl-4-(3-nitrophenyl)-pyridazine-3,5-dicarboxylic acid di-(3-chloroanilide) and 1,4-dihydro-6-methyl-4-(3-nitrophenyl)-pyridazine-3,5-dicarboxylic acid dipiperazide.

The new compounds have a broad and diverse pharmacological action spectrum.

In detail, the following main actions are demonstrable in animal experiments:

(1) On parenteral, oral and perlingual administration the compounds produce a distinct and long-lasting dilation of the coronary vessels. This action on the coronary vessels is intensified by a simultaneous nitrite-like effect of reducing the load on the heart. They influence or modify the heart metabolism in the sense of an energy saving.

(2) The excitability of the stimulus formation and excitation conduction system within the heart is lowered, so that an anti-fibrillation action demonstrable at therapeutic doses results.

(3) The tone of the smooth muscle of the vessels is greatly reduced under the action of the compounds. This vascular-spasmolytic action can take place in the entire vascular system or can manifest itself more or less isolatedly in circumscribed vascular regions (such as, for example, the central nervous system).

(4) The compounds lower the blood pressure of hypertonic animals and can thus be used as anti-nypertensive agents.

(5) The compounds have strongly muscular-spasmolytic actions which manifest themselves on the smooth muscle of the gastro-intestinal tract, the urogenital tract and the respiratory system.

(6) The compounds have an anti-inflammatory action.

As stated above, the invention also relates to the use in medicine of the compounds of the invention.

The present invention provides pharmaceutical compositions containing as active ingredient a compound of the invention in admixture with an inert solid or liquid diluent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents or syrups.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents. e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carrirs, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

Examples of preferred excipients are water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid excipients, such as, for example, natural rock powders (for example kaolins, aluminas, talc and chalk), synthetic rock powders (for example highly disperse silica and silicates) and sugars (for example sucrose, lactose and glucose), emulsifiers, such as non-ionic and anionic emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate); and in the case of oral use the tablets preferably also contain, in addition to the excipients mentioned, preferred additives such as sodium citrate, calcium carbonate and dicalcium phosphate, together with e.g. starch, preferably potato starch, and gelatine.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.5 to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for intravenous administration of the medicaments of the invention is 2.5 to 250 mg of active ingredient and for oral administration is 5 to 250 mg of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), or rectally, preferably orally or parenterally, especially perlingually or intravenously. Preferred pharmaceutical compositions and medicaments are therefore those adapted for administration such as oral and parenteral administration. Administration in the method of the invention is preferably oral or parenteral administration.

In general it has proved advantageous to administer intravenously amounts of from 0.001 mg to 10 mg/kg, preferably 0.05 to 5 mg/kg of body weight per day, or to administer orally from 0.01 to 20 mg/kg, preferably from 0.1 mg to 5 mg/kg of body weight per day, to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The preparation of compounds according to the present invention will now be illustrated by the following Examples.

EXAMPLE 1

1,4-Dihydro-6-methyl-4-phenyl-pyridazine-3,5-dicarboxylic acid dimethyl ester

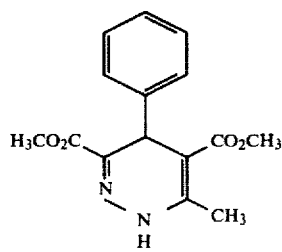

Dry ozone is passed, in excess, into a solution of 69.0 g (0.2 mol) of the sodium salt of 2-acetyl-4-aci-nitro-3-phenyl-glutaric acid dimethyl ester in 300 ml of absolute methanol at −78° C. until the solution becomes blue-coloured. After 30 minutes, the ozone is removed by passing dry nitrogen in and the mixture is warmed to −20°, under nitrogen. 10 g (0.2 mol) of hydrazine hydrate in 50 ml of absolute methanol are added dropwise and the mixture is stirred at room temperature for 12 hours. For working up, the methanol is distilled off in vacuo, the residue is taken up in chloroform and insoluble material is filtered off. The chloroform is distilled off from the filtrate and, after adding a little isopropanol to the residue, the product slowly crystallises out. Melting point: 187°.

Yield: 47% of theory.

EXAMPLE 2

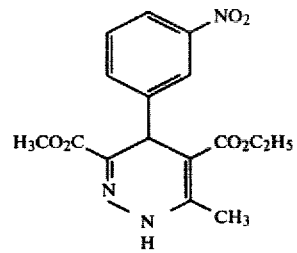

1,4-Dihydro-6-methyl-4-(3-nitrophenyl)-pyridazine-3,5-dicarboxylic acid 5-ethyl 3-methyl ester of melting point 176° (from isopropanol, after chromatography over silica gel using $CHCl_3$/MeOH) is obtained analogously to Example 1 by reacting 0.2 mol of the sodium salt of 2-acetyl-4-aci-nitro-3-(3-nitrophenyl)-glutaric acid 1-ethyl 5-methyl ester with excess ozone and 0.2 mol of hydrazine hydrate.

Yield: 43% of theory.

EXAMPLE 3

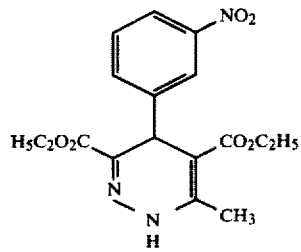

1,4-Dihydro-6-methyl-4-(3-nitrophenyl)-pyridazine-3,5-dicarboxylic acid diethyl ester of melting point 147° (methanol) is obtained analogously to Example 1 by reacting 0.2 mol of the sodium salt of 2-acetyl-4-aci-nitro-3-(3-nitrophenyl)-glutaric acid diethyl ester with excess ozone and 0.2 mol of hydrazine hydrate.

Yield: 72.8% of theory.

EXAMPLE 4

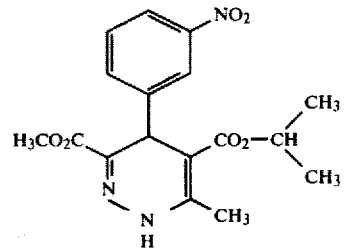

1,4-Dihydro-6-methyl-4-(3-nitrophenyl)-pyridazine-3,5-dicarboxylic acid 5-isopropyl 3-methyl ester of melting point 193° C. (from isopropanol, after silica gel chromatography) is obtained analogously to Example 1 by reacting 0.2 mol of the sodium salt of 2-acetyl-4-aci-nitro-3-(3-nitrophenyl)-glutaric acid 1-isopropyl 5-methyl ester with excess ozone and 0.2 mol of hydrazine hydrate.

EXAMPLE 5

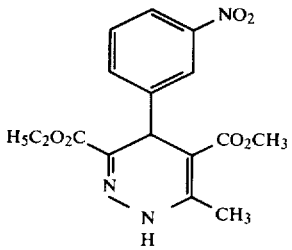

1,4-Dihydro-6-methyl-4-(3-nitrophenyl)-pyridazine-3,5-dicarboxylic acid 3-ethyl 5-methyl ester of melting point 174° (from isopropanol) is obtained analogously to Example 1 by reacting 0.2 mol of the sodium salt of 2-acetyl-4-aci-nitro-3-(3-nitrophenyl)-glutaric acid 5-ethyl 1-methyl ester with excess ozone and 0.2 mol of hydrazine hydrate.
Yield: 55% of theory.

EXAMPLE 6

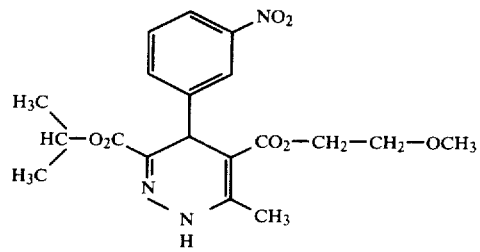

1,4-Dihydro-6-methyl-4-(3-nitrophenyl)-pyridazine-3,5-dicarboxylic acid 3-isopropyl 5-($\beta$-methoxyethyl) ester of melting point 146°–148° (from isopropanol, after silica gel chromatography) is obtained analogously to Example 1 by reacting 0.2 mol of the sodium salt of 2-acetyl-4-aci-nitro-3-(3-nitrophenyl)-glutaric acid 1-($\beta$-methoxyethyl) 5-isopropyl ester with excess ozone and 0.2 mol of hydrazine hydrate.
Yield: 19% of theory.

EXAMPLE 7

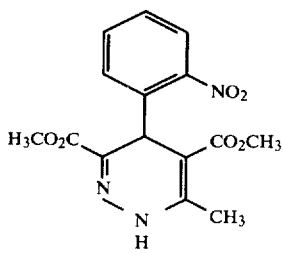

1,4-Dihydro-6-methyl-4-(2-nitrophenyl)-pyridazine-3,5-dicarboxylic acid dimethyl ester of melting point 203°–205° (from ethanol, after silica gel chromatography) is obtained analogously to Example 1 by reacting 0.2 mol of the sodium salt of 2-acetyl-4-aci-nitro-3-(2-nitrophenyl)-glutaric acid dimethyl ester with excess ozone and 0.2 mol of hydrazine hydrate.
Yield: 42% of theory.

EXAMPLE 8

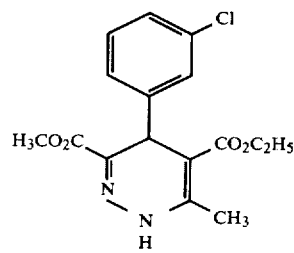

4-(3-Chlorophenyl)-1,4-dihydro-6-methyl-pyridazine-3,5-dicarboxylic acid 5-ethyl 3-methyl ester of melting point 139° (from methanol, after silica gel chromatography) is obtained analogously to Example 1 by reacting 0.2 mol of the sodium salts of 2-acetyl-4-aci-nitro-3-(3-chlorophenyl)-glutaric acid 1-ethyl 5-methyl ester with excess ozone and 0.2 mol of hydrazine hydrate.
Yield: 51% of theory.

EXAMPLE 9

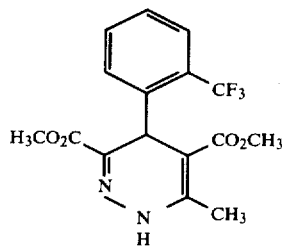

1,4-Dihydro-6-methyl-4-(2-trifluoromethylphenyl)-pyridazine-3,5-dicarboxylic acid dimethyl ester of melting point 205° (methanol) is obtained analogously to Example 1 by reacting 0.1 mol of the sodium salt of 2-acetyl-4-acinitro-3-(2-trifluoromethylphenyl)-glutaric acid dimethyl ester with excess ozone and 0.1 mol of hydrazine hydrate.
Yield: 51% of theory.

EXAMPLE 10

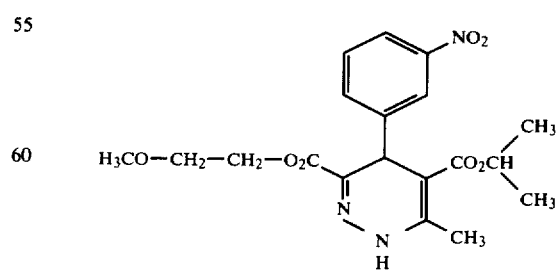

1,4-Dihydro-6-methyl-4-(3-nitrophenyl)-pyridazine-3,5-dicarboxylic acid 5-isopropyl 3-($\beta$-methoxyethyl) ester of melting point 165° (isopropanol) is obtained analogously to Example 1 by reacting 0.1 mol of the sodium salt of 2-acetyl-4-aci-nitro-3-(3-nitrophenyl)-glutaric acid 1-isopropyl 5-(β-methoxyethyl) ester with excess ozone and 0.1 mol of hydrazine hydrate.

Yield: 42% of theory.

EXAMPLE 11

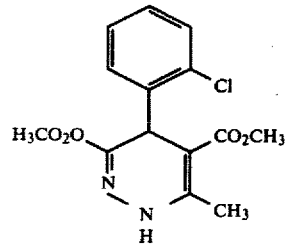

4,(2-Chlorophenyl)-1,4-dihydro-6-methylpyridazine-3,5-dicarboxylic acid dimethyl ester of melting point 177° (ethanol) is obtained analogously to Example 1 by reacting 0.2 mol of the sodium salt of 2-acetyl-4-aci-nitro-3-(2-chlorophenyl)-glutaric acid dimethyl ester ozone and 0.2 mol of hydrazine hydrate.

Yield: 62% of theory.

EXAMPLE 12

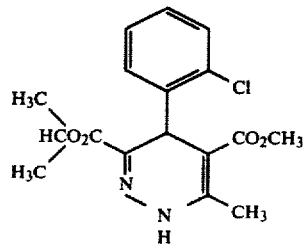

4-(2-Chlorophenyl)-1,4-dihydro-6-methyl-pyridazine-3,5-dicarboxylic acid 3-isopropyl 5-methyl ester of melting point 166° (from ethanol, after column chromatography) is obtained analogously to Example 1 by reacting 0.1 mol of the sodium salt of 2-acetyl-4-aci-nitro-3-(2-chlorphenyl)-glutaric acid 1-methyl 5-isopropyl ester with excess ozone and 0.1 mol of hydrazine hydrate.

Yield: 38% of theory.

EXAMPLE 13

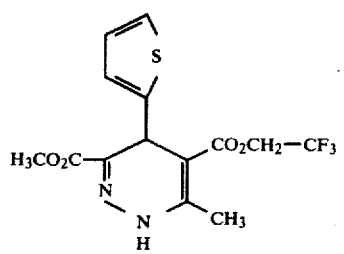

1,4-Dihydro-6-methyl-4-thien-2-yl-pyridazine-3,5-dicarboxylic acid 3-methyl 5-(β-trifluoroethyl) ester of melting point 151° C. (from ethanol, after column chromatography) is obtained analogously to Example 1 by reaction 0.2 mol of the sodium salt of 2-acetyl-4-aci-nitro-3-thien-2-yl-glutaric acid 5-methyl 1-(β-trifluoroethyl) ester with 0.2 mol of ozone and 0.2 mol of hydrazine hydrate.

Yield: 29% of theory.

EXAMPLE 14

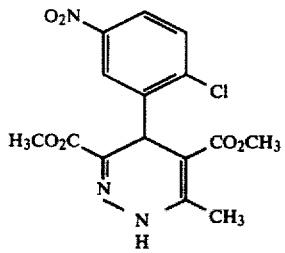

4-(2-Chloro-5-nitrophenyl)-1,4-dihydro-6-methyl-pyridazine-3,5-dicarboxylic acid dimethyl ester of melting point 193°-4° (methanol) is obtained analogously to Example 1 by reacting 0.2 mol of the sodium salt of 2-acetyl-4-aci-nitro-3-(2-chloro-5-nitrophenyl)-glutaric acid dimethyl ester with excess ozone and 0.2 mol of hydrazine hydrate.

Yield: 68% of theory.

EXAMPLE 15

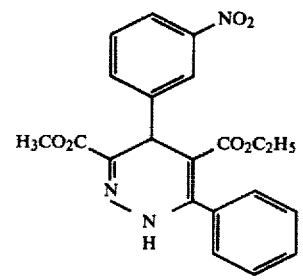

1,4-Dihydro-4-(3-nitrophenyl)-6-phenyl-pyridazine-3,5-dicarboxylic acid 5-ethyl 4-methyl ester of melting point 187° C. (methanol) is obtained analogously to Example 1 by reacting 0.2 mol of the sodium salt of 4-aci-nitro-2-benzoyl-3-(3-nitrophenyl)-glutaric acid 1-ethyl 5-methyl ester with excess ozone and 0.2 mol of hydrazine hydrate.

Yield: 37% of theory.

EXAMPLE 16

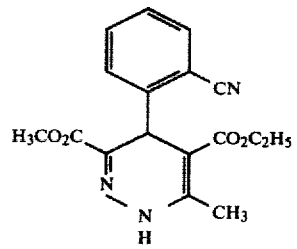

4-(2-Cyanophenyl)-1,4-dihydro-6-methylpyridazine-3,5-dicarboxylic acid 5-ethyl 3-methyl ester of melting point 199° (ethanol) is obtained analogously to Example 1 by reacting 0.2 mol of the sodium salt of 2-acetyl-4-aci-nitro-3-(2-cyanophenyl)-glutaric acid 2-ethyl 5- methyl ester with excess ozone and 0.2 mol of hydrazine hydrate.

Yield: 57% of theory.

EXAMPLE 17

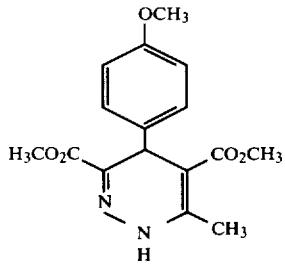

1,4-Dihydro-4-(4-methoxyphenyl)-6-methylpyridazine-3,5-dicarboxylic acid dimethyl ester of melting point 154° (isopropanol) is obtained analogously to Example 1 by reacting 0.1 mol of the sodium salt of 2-acetyl-4-aci-nitro-3-(4-methoxyphenyl)-glutaric acid dimethyl ester with excess ozone and 0.1 mol of hydrazine hydrate.

Yield: 51% of theory.

EXAMPLE 18

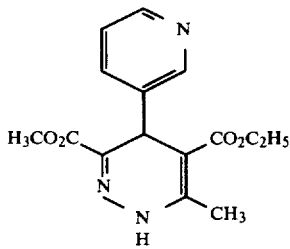

1,4-Dihydro-6-methyl-4-pyrid-3-yl-pyridazine-3,5-dicarboxylic acid 5-ethyl 3-methyl ester of melting point 179° (from isopropanol, after column chromatography) is obtained analogously to Example 1 by reacting 0.2 mol of the sodium salt of 2-acetyl-4-aci-nitro-3-pyrid-3-yl-glutaric acid 1-ethyl 5-methyl ester with 0.2 mol of ozone and 0.2 mol of hydrazine hydrate.

Yield: 38% of theory.

EXAMPLE 19

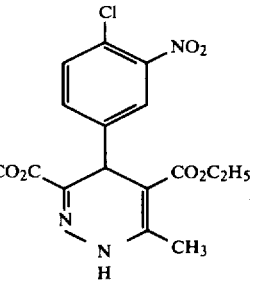

1,4-Dihydro-6-methyl-4-(4-nitrophenyl)-pyridazine-3,5-dicarboxylic acid 5-ethyl 3-methyl ester of melting point 205°-6° (methanol) is obtained analogously to Example 1 by reacting 0.2 mol of the sodium salt of 2-acetyl-4-aci-nitro-3-(4-nitrophenyl)-glutaric acid 1-ethyl 5-methyl ester with excess ozone and 0.2 mol of hydrazine hydrate.

Yield: 61% of theory.

EXAMPLE 20

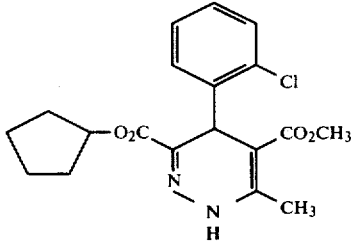

4-(2-Chlorophenyl)-1,4-dihydro-6-methyl-pyridazine-3,5-dicarboxylic acid 3-cyclopentyl 5-methyl ester of melting point 152° (isopropanol) is obtained analogously to Example 1 by reacting 0.1 mol of the sodium salt of 2-acetyl-4-aci-nitro-3-(2-chlorophenyl)-glutaric acid 5-cyclopentyl 1-methyl ester with excess ozone and 0.1 mol of hydrazine hydrate.

Yield: 46: of theory.

EXAMPLE 21

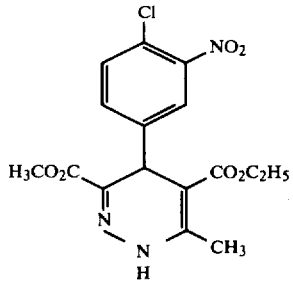

4-(4-Chloro-3-nitrophenyl)-1,4-dihydro-6-methyl-pyridazine-3,5-carboxylic acid 5-ethyl 3-methyl ester of melting point 169° (methanol) is obtained analogously to Example 1 by reacting 0.2 mol of the sodium salt of 2-acetyl-4-aci-nitro-3-(4-chloro-3-nitrophenyl)-glutaric acid 1-ethyl 5-methyl ester with excess ozone and 0.2 mol of hydrazine.

Yield: 58% of theory.

EXAMPLE 22

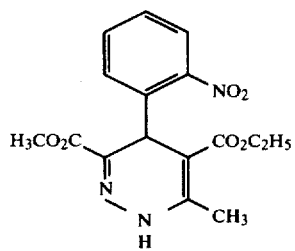

1,4-Dihydro-6-methyl-4-(2-nitrophenyl)-pyridazine-3,5-dicarboxylic acid 5-ethyl 3-methyl ester of melting point 168°-9° (from isopropanol, after silica gel chromatography) is obtained analogously to Example 1 by reacting 0.2 mol of the sodium salt of 2-acetyl-4-aci-nitro-3-(2-nitrophenyl)-glutaric acid 1-ethyl 5-methyl ester with excess ozone and 0.2 mol of hydrazine hydrate.

Yield: 39% of theory.

EXAMPLE 23

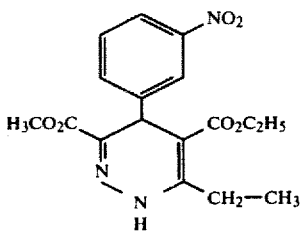

6-Ethyl-1,4-dihydro-4-(3-nitrophenyl)-pyridazine-3,5-dicarboxylic acid 5-ethyl 3-methyl ester of melting point 139° (ethanol) is obtained analogously to Example 1 by reacting 0.1 mol of the sodium salt of 4-aci-nitro-3-(3-nitrophenyl)-1-propionylglutaric acid 1-ethyl 5-methyl ester with excess ozone and 0.1 mol of hydrazine hydrate.

Yield: 55% of theory.

EXAMPLE 24

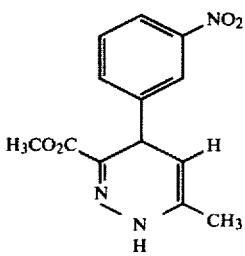

1,4-Dihydro-6-methyl-4-(3-nitrophenyl)-pyridazine-3-carboxylic acid of melting point 149° (from ethanol, after silica gel chromatography) is obtained analogously to Example 1 by reacting 0.1 mol of the sodium salt of 2-aci-nitro-5-oxo-3-(3-nitrophenyl)-hexanoic acid methyl ester with excess ozone and 0.1 mol of hydrazine hydrate.

Yield: 72% of theory.

EXAMPLE 25

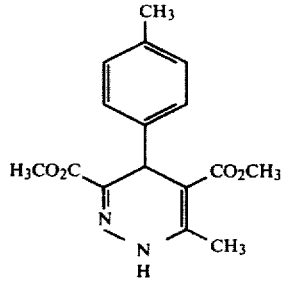

1,4-Dihydro-6-methyl-4-tolu-4-yl-pyridazine-3,5-dicarboxylic acid dimethyl ester of melting point 180° C. (from ethanol, after silica gel chromatography) is obtained analogously to Example 1 by reacting 0.2 mol of the sodium salt of 2-acetyl-4-aci-nitro-3-tolu-4-yl-glutaric acid dimethyl ester with excess ozone and 0.2 mol of hydrazine hydrate.

Yield: 62% of theory.

EXAMPLE 26

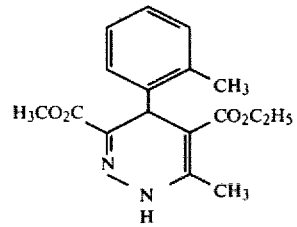

1,4-Dihydro-6-methyl-4-tolu-2-yl-pyridazine-3,5-dicarboxylic acid 5-ethyl 3-methyl ester of melting point 165° (from ethanol, after silica gel chromatography) is obtained analogously to Example 1 by reacting 0.2 mol of the sodium salt of 2-acetyl-4-aci-nitro-3-tolu-2-yl-glutaric acid 3-ethyl 5-methyl ester with excess ozone and 0.2 mol of hydrazine hydrate.

Yield: 49% of theory.

EXAMPLE 27

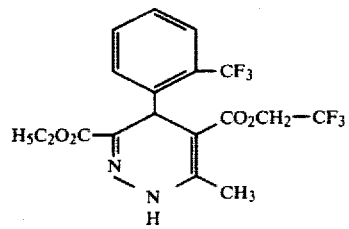

1,4-Dihydro-6-methyl-4-(2-trifluoromethylphenyl)-pyridazine-3,5-dicarboxylic acid 3-ethyl 5-($\beta$-trifluoroethyl) ester of melting point 197° C. (from isopropanol, after silica gel chromatography) is obtained analogously to Example 1 by reacting 0.2 mol of the sodium salt of 2-acetyl-4-aci-nitro-3-(2-trifluoromethylphenyl)-glutaric acid 5-ethyl 1-($\beta$-trifluoroethyl) ester with excess ozone and 0.2 mol of hydrazine hydrate.

EXAMPLE 28

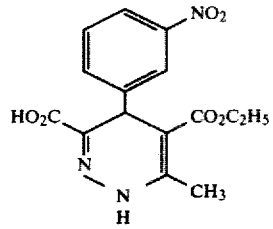

0.1 mol of 1,4-dihydro-6-methyl-4-(3-nitrophenyl)-pyridazine-3,5-dicarboxylic acid diethyl ester are heated under reflux with 0.105 mol of KOH in 150 ml of 50 percent strength aqueous ethanol for 8 hours. The ethanol is distilled off in vacuo, the aqueous residue is extracted with chloroform, the product phase is acidified to pH 1 and the product was extracted with chloroform. The organic phase is concentrated and 1,4-dihydro-6-methyl-4-(3-nitrophenyl)-pyridazine-3,5-dicarboxylic acid 5 ethyl ester of melting point 205° C. (decomposition) crystallised from the residue with a little ethanol.

Yield: 91% of theory.

EXAMPLE 29

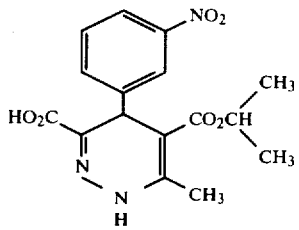

0.1 mol of 1,4-dihydro-6-methyl-4-(3-nitrophenyl)-pyridazine-3,5-dicarboxylic acid 5-isopropyl 3-methyl ester is saponified with 0.105 mol of KOH analogously to Example 28 to give 1,4-dihydro-6-methyl-4-(3-nitrophenyl)-pyridazine-3,5-dicarboxylic acid 5-isopropyl ester. Melting point 195° C. (ethanol)

Yield: 92% of theory.

EXAMPLE 30

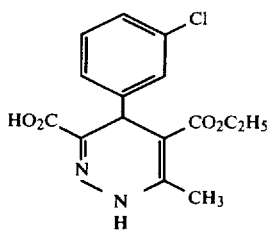

0.1 mol of 4-(3-chlorophenyl)-1,4-dihydro-6-methyl-pyridazine-3,5-dicarboxylic acid 5-ethyl 3-methyl ester is saponified with 0.105 mol of KOH analogously to Example 28 to give 4-(3-chlorophenyl)-1,4-dihydro-6-methyl-pyridazine-3,5-dicarboxylic acid 5-ethyl ester. Melting point 182° C. (ethanol).

Yield: 89% of theory.

EXAMPLE 31

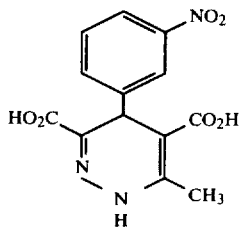

0.1 mol of 1,4-dihydro-6-methyl-4-(3-nitrophenyl)-pyridazine-3,5-dicarboxylic acid diethyl ester is saponified with 0.25 mol of KOH analogously to Example 28 to give 1,4-dihydro-6-methyl-4-(3-nitrophenyl)-pyridazine-3,5-dicarboxylic acid. Melting point 169° C. (decomposition).

Yield: 71% of theory.

EXAMPLE 32

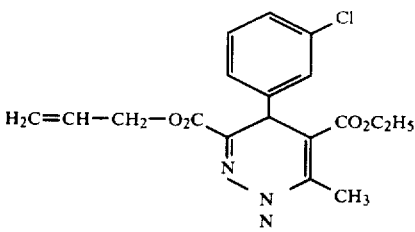

0.1 mol of 4-(3-chlorophenyl)-1,4-dihydro-6-methyl-pyridazine-3,5-dicarboxylic acid 5-ethyl ester is heated under reflux in 150 ml of absolute allyl alcohol for 18 hours, with the addition of a trace of p-toluenesulphonic acid. The alcohol is distilled off, the residue is dissolved in chloroform and the chloroform solution is washed with sodium bicarbonate solution. After evaporating off the chloroform, 4-(3-chlorophenyl)-1,4-dihydro-6-methyl-pyridazine-3,5-dicarboxylic acid 3-allyl 5-ethyl ester, melting point 125° C., crystallised from a little ethanol.

Yield: 82% of theory.

EXAMPLE 33

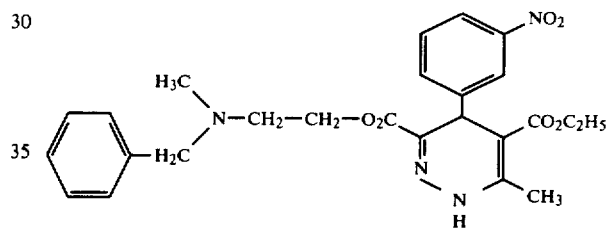

1,4-Dihydro-6-methyl-4-(3-nitrophenyl)-pyridazine-3,5-dicarboxylic acid 3-($\beta$-N-benzyl-N-methylaminoethyl) 5-ethyl ester of melting point 192° C. (methanol) is obtained analogously to Example 32 from 0.1 mol of 1,4-dihydro-6-methyl-4-(3-nitrophenyl)-pyridazine-3,5-dicarboxylic acid 5-ethyl ester after heating to 100° C. in 100 ml of $\beta$-N-benzyl-N-methylaminoethanol for 20 hours, with the addition of a trace of p-toluenesulphonic acid.

Yield: 57% of theory.

EXAMPLE 34

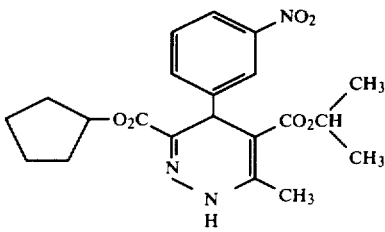

1,4-Dihydro-6-methyl-4-(3-nitrophenyl)-pyridazine-3,5-dicarboxylic acid 3-cyclopentyl 5-isopropyl ester of melting point 141° C. (from methanol, after silica gel chromatograph) is obtained analogously to Example 32 from 0.1 mol of 1,4-dihydro-6-methyl-4-(2-nitrophenyl)-pyridazine-3,5-dicarboxylic acid 5-isopropyl ester after heating to 100° C. in 100 ml of cyclopentanol for 12 hours, with the addition of 1 ml of concentrated sulphuric acid.

Yield: 69% of theory.

EXAMPLE 35

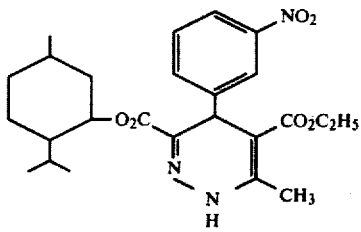

1,4-Dihydro-6-methyl-4-(3-nitrophenyl)-pyridazine-3,5-dicarboxylic acid 5-ethyl 3-1-menthyl ester of melting point 136° C. (ethanol) is obtained analogously to Example 32 from 0.1 mol of 1,4-dihydro-6-methyl-4-(3-nitrophenyl)-pyridazine-3,5-dicarboxylic acid 5-ethyl ester after heating to 100° C. in 30 g of 1-menthol for 12 hours, with the addition of 0.5 ml of concentrated sulphuric acid.

Yield: 42% of theory.

EXAMPLE 36

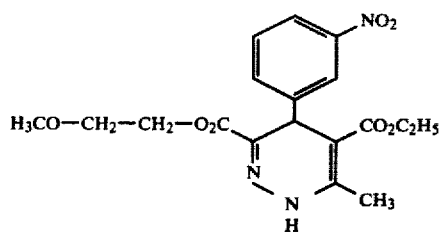

1,4-Dihydro-6-methyl-4-(3-nitrophenyl)-pyridazine-3,5-dicarboxylic acid 5-ethyl 3-($\beta$-methoxyethyl) ester of melting point 118° C. (isopropanol) is obtained analogously to Example 32 from 0.1 mol of 1,4-dihydro-6-methyl-4-(3-nitrophenyl)-pyridazine-3,5-dicarboxylic acid diethyl ester after heating in 150 ml of boiling methoxyethanol for 12 hours, with the addition of a trace of p-toluenesulphonic acid.

Yield: 79% theory.

EXAMPLE 37

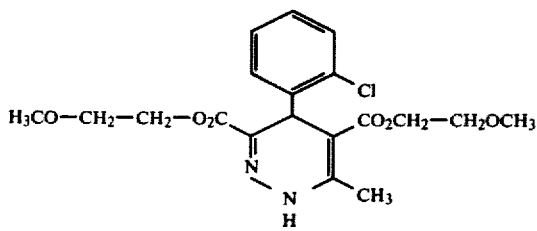

4-(2-Chlorophenyl)-1,4-dihydro-6-methyl-pyridazine-3,5-dicarboxylic acid di-($\beta$-methoxyethyl) ester of melting point 117° C . (from isopropanol) is obtained analogously to Example 32 from 0.1 mol of 1,4-dihydro-6-methyl-4-(3-nitrophenyl)-pyridazine-3,5-dicarboxylic acid diethyl ester after heating in boiling methoxyethanol for 48 hours, with the addition of a trace of p-toluenesulphonic acid.

Yield: 54% of theory.

EXAMPLE 38

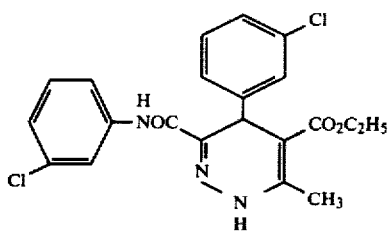

0.05 mol of dicyclohexylcarbodiimide in 20 ml of methylene chloride are added to 0.05 mol of 4-(3-chlorophenyl)-1,4-dihydro-6-methyl-pyridazine-3,5-dicarboxylic acid 5-ethyl ester and 0.06 mol of 3-chloroaniline in 50 ml of methylene chloride, whilst cooling with ice, and the mixture is stirred at room temperature for 12 hours. The precipitate is filtered off, the organic phase is washed with sodium bicarbonate solution and concentrated and the resulting 3-(3-chlorophenylcarbamoyl)-4-(3-chlorophenyl)-1,4-dihydro-6-methyl-pyridazine-5-carboxylic acid ethyl ester is crystallised from ethanol. Melting point: 189° C.

Yield: 79% of theory.

EXAMPLE 39

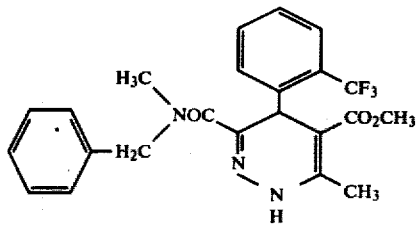

3-(Benzyl-methylcarbamoyl)-1,4-dihydro-6-methyl-4-(2-trifluoromethylphenyl)-pyridazine-5-carboxylic acid methyl ester of melting point 197° C. (ethanol) is obtained analogously to Example 38 by reacting 0.05 mol of 1,4-dihydro-6-methyl-4-(2-trifluoromethylphenyl)pyridazine-3,5-dicarboxylic acid 5-methyl ester with 0.06 mol of benzyl-methylamine and 0.05 mol of dicyclohexylcarbodiimide.

Yield: 71% of theory.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the animal's body to the active compound.

What is claimed is:

1. A compound of the formula

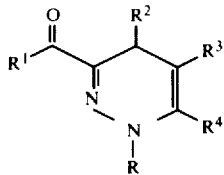

in which
- R is a hydrogen atom or a straight-chain or branched alkyl radical having 1 to 8 carbon atoms which is optionally interrupted in the chain by one or two oxygen atoms, or a mono- or bi-cyclic carbocyclic aryl or ar-$C_1$-$C_4$-alkyl radical,
- $R^1$ is a group of the formula

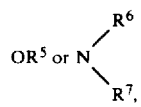

in which
- $R^5$ is a hydrogen atom or a straight-chain, branched or cyclic, saturated or unsaturated aliphatic hydrocarbon radical, having up to 8 carbon atoms, which is optionally interrupted in the saturated or unsaturated aliphatic chain by 1 or 2 oxygen or sulphur atoms and which is optionally substituted by a hydroxyl or halogen; or by a phenoxy or phenyl group which is optionally substituted by a halogen, cyano amino, $C_1$-$C_8$ alkylamino, $C_1$-$C_8$-alkoxy, $C_1$-$C_8$-alkyl, trifluoromethyl or nitro, or by an α-, β- or γ-pyridyl group or by an amino group, this amino group optionally carrying either hydrogen and one substituent or two identical or different substituents selected from $C_1$-$C_8$-alkyl, $C_1$-$C_8$-alkoxy-alkyl, $C_1$-$C_8$-alkyl, a mono- or bi-cyclic carbocyclic aryl and a mono- or bi-cyclic carbocyclic ar-$C_1$-$C_4$-alkyl, or
- $R^5$ is a mono- or bi-cyclic carbocyclic aryl group which is optionally substituted by one or two identical or different substituents selected from $C_1$-$C_8$-alkyl, $C_1$-$C_8$-alkoxy, a mono- or bi-cyclic carbocyclic aryl, a mono- or bi-cyclic carbocyclic ar-$C_1$-$C_4$-alkyl, halogen, nitro, cyano, trifluoromethyl, trifluoromethoxy, amino and mono-$C_1$-$C_8$ and di-$C_1$-$C_8$-alkylamino,
- $R^6$ is a hydrogen atom or a $C_1$-$C_8$-alkyl, a mono- or bi-cyclic carbocyclic aryl, a mono- or bi-cyclic carbocyclic ar-$C_1$-$C_4$-alkyl, thienyl, furyl or pyridyl radical which optionally carries 1 to 3 identical or different substituents selected from halogen, nitro, cyano, trifluoromethyl, trifluoromethoxy, $C_1$-$C_8$-alkoxy, $C_1$-$C_8$-alkyl and di-$C_1$-$C_8$-alkylamino and
- $R^7$ is a hydrogen atom or an amino or mono-$C_1$-$C_8$- or di-$C_1$-$C_8$-alkylamino group, or has a meaning given for radical $R^6$, without being identical to $R^6$,
- $R^2$ is a mono- or bi-cyclic carbocyclic aryl radical or a thienyl, furyl, pyrryl, pyrazolyl, imidazolyl, oxazolyl, isooxazolyl, thiazolyl, pyridyl, pyridazinyl, pyrimidyl, pyrazinyl, quinolyl, isoquinolyl, indolyl, benzimidazolyl, quinazolyl or quinoxalyl radicals, said aryl radical and said heterocyclic radicals optionally containing 1 to 3 identical or different substituents selected from phenyl, $C_1$-$C_8$-alkyl, $C_1$-$C_8$-alkoxy, halogen, trifluoromethyl, cyano, trifluoromethoxy, hydroxyl, nitro, azido, carboxyl, carb $C_1$-$C_8$-alkoxy, carboxamido, sulphonamido, $SO_2$-$C_1$-$C_8$-alkyl and $SO_2$-trifluoroalkyl,
- $R^3$ is a hydrogen atom or a group of the formula $COR^8$, in which
- $R^8$ is an $C_1$-$C_8$-alkyl, a mono- or bi-cyclic carbocyclic aryl or a mono- or bi-cyclic carbocyclic ar-$C_1$-$C_4$-alkyl aralkyl radical or a group of the formula $OR^9$, in which
- $R^9$ has a meaning given for radical $R^5$, but need not be identical to $R^5$, and
- $R^4$ is a straight-chain or branched alkyl radical having 1 to 8 carbon atoms in which a hydrogen is replaced by a hydroxyl group, or a polyfluoro $C_1$-$C_8$-alkyl radical or a phenyl, benzyl, thienyl, furyl, pyrryl or pyridyl radical.

2. A compound according to claim 1, in which
- R denotes a hydrogen atom or a methyl, phenyl or benzyl radical,
- $R^1$ denotes a group of the formula

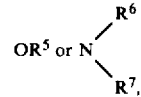

in which
- $R^5$ denotes a straight-chain, branched or cyclic alkyl, alkenyl or alkinyl radical with up to 8 carbon atoms, the alkyl or alkylene chain optionally being interrupted by an oxygen and/or sulphur atom and/or substituted by halogen, phenoxy, phenyl, halogenophenyl, nitrophenyl, pyridyl, furyl or thienyl, or denotes a pyridyl, furyl, thienyl or a phenyl radical which is optionally substituted by one or two identical or different substituents selected from halogen, nitro, cyano, trifluoromethyl, trifluoromethoxy and alkyl or alkoxy with in each case 1 to 4 carbon atoms,
- $R^6$ denotes a hydrogen atom or a methyl, ethyl, benzyl, pyridyl or phenyl radical which is optionally substituted by one or two identical or different substituents selected from halogen, nitro, cyano, trifluoromethyl and trifluoromethoxy,
- $R^7$ denotes a hydrogen atom or an amino or mono- or dialkylamino group with 1 to 4 carbon atoms per alkyl group, or has a meaning given for radical $R^6$, without being identical to $R^6$;
- $R^2$ denotes a phenyl radical which is optionally substituted by one or two identical or different substituents selected from nitro, halogen, azido, cyano, trifluoromethyl, trifluoromethoxy and alkyl or alkoxy with in each case 1 to 4 carbon atoms, or denotes a pyridyl, thienyl or furyl radical,
- $R^3$ denotes hydrogen or a group of the formula $COR^8$, in which
- $R^8$ denotes an alkyl radical with 1 to 4 carbon atoms or an aryl radical, or
- $R^8$ denotes a group of the formula $OR^9$, in which
- $R^9$ has a meaning given for radical $R^5$, but must not be identical to $R^5$, and
- $R^4$ denotes an alkyl radical with 1 to 2 carbon atoms, or denotes a phenyl, benzyl, pyridyl or thienyl radical.

3. A compound according to claim 2, in which
$R^5$ denotes a straight-chain, branched or cyclic alkyl, alkenyl or alkinyl radical with up to 8 carbon atoms, the alkyl or alkylene chain optionally being interrupted by an oxygen and/or sulphur atom and/or substituted by one or more fluorine atoms or denotes a pyridyl, furyl, thienyl which is optionally substituted by one or two identical or different substituents as specified in claim 2, in which at least one is alkyl or alkoxy with in each case 1 or 2 carbon atoms, $R^6$ has the same meaning as in claim 2, $R^7$ denotes a mono- or dialkylamino group with 1 or 2 carbon atoms per alkyl group, or $R^2$ denotes a phenyl radical optionally substituted by one or two identical or different substituents as specified in claim 2, in which at least one is alkyl or alkoxy with 1 or 2 carbon atoms, and $R^8$ and $R^4$ have the same meaning as in claim 2.

4. A compound according to claim 1 of the formula

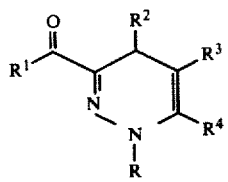

(I)

in which

R denotes a hydrogen atom or a methyl, phenyl or benzyl radical $R^1$ denotes a group of the formula

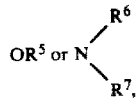

in which $R^5$ denotes hydrogen or a straight-chain branched or cyclic alkyl or alkenyl radical with up to 8 carbon atoms, the alkyl or alkenyl chain optionally being interrupted by an oxygen and/or sulphur atom and optionally substituted by one or more fluorine atoms, or denotes a pyridyl or phenyl radical which phenyl radical is optionally substituted by one or two identical or different substituents elected from halogen, nitro, cyano, trifluoromethyl or trifluoromethoxy, $R^6$ denotes a hydrogen atom or a methyl, ethyl, benzyl or phenyl radical which is optionally substituted by one or two identical or different substituents elected from halogen, nitro, cyano, trifluoromethyl and trifluoromethoxy, $R^7$ denotes a hydrogen atom or a methyl, ethyl, benzyl or phenyl radical, $R^2$ denotes a phenyl radical which is optionally substituted by one or two identical or different substituents elected from nitro, halogen, acido, cyano, trifluoromethyl, trifluoromethoxy and alkyl or alkoxy with in each case 1 to 4 carbon atoms, or denotes a pyridyl, thienyl or furyl radical, $R^3$ denotes hydrogen or a group of the formula $COOR^9$ in which $R^9$ has the meaning given for radical $R^5$ but need not be identical to $R^5$ and $R^4$ denotes an alkyl radical with 1 to 2 carbon atoms or a phenyl or benzyl radical.

5. A method of combating hypertension in warm-blooded animals which comprises administering to the animals an antihypertensively effective amount of an active compound according to claim 1 either alone or in admixture with a diluent or in the form of a medicament.

6. A method according to claim 5 in which the active compound is administered intravenously in an amount of 0.001 to 10 mg per kg body weight per day.

7. A method according to claim 6 in which the active compound is administered intravenously in an amount of 0.05 to 5 mg per kg body weight per day.

8. A pharmaceutical composition containing as the active ingredient an antihypertensively effective amount of a compound according to claim 1 in admixture with an inert solid or liquid diluent.

9. A pharmaceutical composition of claim 8 in the form of a sterile or physiologically isotonic aqueous solution.

10. A composition according to claim 8 containing from 0.5 to 90% by weight of the said active ingredient.

11. A medicament in dosage unit form comprising an antihypertensively effective amount of a compound according to claim 1 together with an inert pharmaceutical carrier.

12. A medicament of claim 11 in the form of tablets, pills, dragees, capsules, ampoules or suppositories.

13. A method according to claim 5 in which the active compound is administered orally in an amount of 0.01 to 20 mg per kg body weight per day.

14. A method according to claim 13 in which the active compound is administered orally in an amount of 0.1 to 5 mg per kg body weigh per day.

* * * * *